(12) United States Patent
Kuster

(10) Patent No.: US 11,035,871 B2
(45) Date of Patent: Jun. 15, 2021

(54) TUBE GUIDANCE MEANS FOR A LABORATORY AUTOMATION SYSTEM

(71) Applicant: TECAN TRADING AG, Maennedorf (CH)

(72) Inventor: Martin Kuster, Eschenbach (CH)

(73) Assignee: TECAN TRADING AG, Maennedorf (CH)

( * ) Notice: Subject to any disclaimer, the term of this patent is extended or adjusted under 35 U.S.C. 154(b) by 138 days.

(21) Appl. No.: 16/578,053

(22) Filed: Sep. 20, 2019

(65) Prior Publication Data

US 2020/0110106 A1 Apr. 9, 2020

(30) Foreign Application Priority Data

Oct. 4, 2018 (EP) ..................................... 18198729

(51) Int. Cl.
*G01N 35/10* (2006.01)
*B01L 3/02* (2006.01)
*G01N 35/04* (2006.01)

(52) U.S. Cl.
CPC ........ *G01N 35/1011* (2013.01); *B01L 3/0227* (2013.01); *G01N 35/1081* (2013.01); *G01N 2035/0406* (2013.01)

(58) Field of Classification Search
CPC ........... G01N 35/1011; G01N 35/1085; G01N 2035/0406; B01L 3/0227
See application file for complete search history.

(56) References Cited

U.S. PATENT DOCUMENTS

| 6,382,569 B1 | 5/2002 | Schattner et al. |
| 2013/0138044 A1 | 5/2013 | Schuman et al. |
| 2014/0049144 A1 | 2/2014 | Han et al. |
| 2014/0103171 A1 | 4/2014 | Sutherland et al. |
| 2018/0321268 A1* | 11/2018 | Schacher ............... G01N 35/02 |

\* cited by examiner

*Primary Examiner* — Jennifer Wecker
*Assistant Examiner* — Kathryn Elizabeth Limbaugh
(74) *Attorney, Agent, or Firm* — MH2 Technology Law Group LLP

(57) ABSTRACT

A tube guidance means (36) for a laboratory automation system (10) comprises a plate (40) with a guide opening (38); wherein the guide opening (38) has two partial openings (42) which are separated by a land (46) and which are connected by a slot (44); and wherein the partial openings (42) have cutouts (54) for guiding a tube (32), the cutouts (54) being located opposite each other on edges (52) which face away from each other.

15 Claims, 4 Drawing Sheets

TUBE GUIDANCE MEANS FOR A LABORATORY AUTOMATION SYSTEM

CROSS REFERENCE TO RELATED APPLICATION(S)

This application claims the benefit of and priority to European Patent Application No. 18 198 729.8, filed Oct. 4, 2018, the entire contents of which are incorporated herein by reference.

FIELD OF THE INVENTION

The invention relates to a tube guidance means for a laboratory automation system, to a laboratory automation system component, and to a laboratory automation system.

BACKGROUND OF THE INVENTION

Laboratory automation systems are used to automate activities of a laboratory assistant. For example, samples may be pipetted, mixed with chemicals and/or reagents, and the reactions occurring may be analysed using a laboratory automation system.

The laboratory automation system to this end may have a pipetting device which is connected to a pump by way of tubes. The pipetting device may for example be lowered into test tubes or a pipetting plate, and the pump may aspirate and dispense liquids from these containers with the aid of the tubes. If the pipetting device is mounted in movable manner, the tubes as a rule have to be guided along relatively long stretches by arms and/or housing parts. Therefore the tubes are fixed to different components of the laboratory automation system, for example with clamps. In such case, it is important that the tubes cannot be kinked or damaged when the pipetting device is moved.

SUMMARY OF THE INVENTION

The object of the invention is to lay tubes safely and inexpensively in a laboratory automation system. Further, strain relief on the tubes may be guaranteed with the invention.

This object is achieved by the subject-matter of the independent claims. Further embodiments of the invention will become apparent from the dependent claims and from the following description.

One aspect of the invention relates to a tube guidance means for a laboratory automation system. A laboratory automation system may in this case be an apparatus which is designed to automate pipetting operations.

To this end, the laboratory automation system with a workbench may provide a flat surface on which containers and/or analytical apparatus may be placed. Further, the laboratory automation system may have a pipetting arm which may be mounted in movable manner with respect to the workbench. A pipetting device which may be moved with the pipetting arm may be fastened to the pipetting arm. The pipetting device, which may bear a plurality of pipettes, may be connected by way of a plurality of tubes to a pump which is fastened for example to the workbench.

The tube guidance means may be a constituent of the laboratory automation system and/or be provided by a component of the laboratory automation system, such as a pump casing, a pipetting arm, etc. The tube guidance means may be designed to guide the tubes, fix them at a point of the laboratory automation system and/or deflect them.

According to one embodiment of the invention, the tube guidance means comprises a plate with a guide opening, wherein the guide opening has two partial openings which are separated by a land and which are connected by a slot. The partial openings have cutouts for guiding a tube, the cutouts being located opposite each other on edges which face away from each other.

The plate may be a plastics-material plate or a metal plate. The plate may be a sheet, such as a plastics-material sheet or a metal sheet. The plate may be a plastics-material plate with fibre reinforcement, for example with carbon fibres. The plate may be a casing of a component of the laboratory automation system. The plate may be flat in the vicinity of the tube guidance means. It is possible for the tube guidance means to be arranged in a flat region of an angled plate.

The guide opening comprises two partial openings which are connected together by way of a slot. The guide opening may be produced in a simple manner by punching and/or cutting the plate. It is not necessary to attach further elements for a tube guidance means to the desired points of the laboratory automation system. Thus a saving may be made in terms of material and operating steps.

A tube may be placed through the slot into the guide opening and in particular two cutouts, and pushed behind the land. The land may prevent the tube from dropping out of the guide opening. The land may run transversely to a direction of guidance in which the tubes are guided through the guide opening. The direction of guidance may be defined by two opposing cutouts which are intended for one tube.

The slot may have a width which is somewhat (for example up to 10%) greater than the diameter of a tube. The cutouts and/or the edges thereof may prevent lateral shifting of the tube and/or shifting of the tube along its longitudinal direction. The cutouts may have a width which corresponds to the diameter of a tube.

The cutouts of a partial opening may be arranged next to one another and/or be opened in the same direction. The cutouts of the other partial opening may be opened in the opposite direction.

According to one embodiment of the invention, the slot runs through a centre of the land. The land may be divided in two. For example, two tongue-shaped portions of the land may protrude into the guide opening transversely to the direction of guidance.

According to one embodiment of the invention, the slot runs at one end of the land. The land may be of one piece. For example, a tongue-shaped portion of the land may protrude into the guide opening transversely to the direction of guidance.

According to one embodiment of the invention, the slot runs obliquely to the direction of guidance which is defined by two opposing cutouts for a tube. This may make it more difficult for a tube to drop out of the guide opening once laid.

According to one embodiment of the invention, the slot is curved in a U-shape. This too may make it more difficult for a tube to drop out of the guide opening once laid.

According to one embodiment of the invention, the land widens towards the slot. For example, a tongue of the land which runs transversely to the direction of guidance may be L-shaped or T-shaped at its end. This is a further possible way of making it difficult for a tube to drop out of the guide opening once laid.

According to one embodiment of the invention, the cutouts are arranged in a transverse direction or transversely to the direction of guidance spaced apart from a slot region of the land. The slot region may be a portion of the land in which the slot is present. Thus laid tubes run next to the slot behind the land.

According to one embodiment of the invention, the cutouts widen towards the land. For example, the cutouts may be triangular, oval, parabolic, ellipsoidal and/or polygonal. In general, the cutouts, on the side which faces the land, may be wider than a diameter of a tube and taper with increasing distance from the land, so that their width is less than the diameter of the tube.

According to one embodiment of the invention, the guide opening is arranged in an opening region of the plate which is elevated with respect to a surrounding region. The guide opening and the opening region may be formed in one operating step by punching, laser beam cutting and/or waterjet cutting and/or other methods. Behind the opening region, an additional space may be produced through which the tubes which are clamped behind the land may run, without structural elements behind the plate, which may be a casing, being adversely affected.

According to one embodiment of the invention, the partial openings and the land are arranged in one plane, in particular in a different plane from the plane which is defined by the region which surrounds the opening region. Thus the clamping action of the land on the tube and/or a plurality of tubes may be ensured.

According to one embodiment of the invention, the plate has a plurality of guide openings. Thus tubes may be fixed and guided on the plate along a longer stretch.

According to one embodiment of the invention, the plate has a deflection opening which has two partial openings arranged obliquely to each other which are separated by a land and which are connected by a slot. The deflection opening does not have to have any cutouts which fix the tubes in a direction of movement. Nevertheless, the tubes may be held on the plate by the land.

It is to be understood that constituents of the deflection opening, like those of the guide opening, may be arranged and/or formed relative to each other. For example, the guide opening may have cutouts. It is also possible for the slot to be arranged in the centre or at one end of the land, etc.

According to one embodiment of the invention, the deflection opening is arranged in an opening region of the plate which is elevated with respect to a surrounding region, the partial openings of the deflection opening being arranged in a transitional region between the opening region and the surrounding region, so that edges of the partial openings are arranged in different planes. In this manner, the land no longer clamps the tubes and the tubes may slide through the deflection opening.

According to one embodiment of the invention, the slot of the deflection opening runs through the transitional region and the opening region. This may prevent the tubes from dropping out of the deflection opening.

A further aspect of the invention relates to a component for a laboratory automation system. A component in this case may be a constituent of the laboratory automation system which has a housing with a plate. For example, the component may be a pump, a pipetting arm or an arm suspension means of the pipetting arm.

According to one embodiment of the invention, the component comprises a tube guidance means and a plurality of tubes which are guided through the guide opening of the tube guidance means. The plate with the guide opening may be a casing of the component. Each of the tubes may run through the two partial openings and behind the land, and be placed in two opposing cutouts in each case.

A further aspect of the invention relates to a laboratory automation system.

According to one embodiment of the invention, the laboratory automation system comprises a workbench, a rail fastened to the workbench, an arm fastened in movable manner to the rail by way of an arm suspension means, to which arm a pipetting device is fastened above the workbench, and a pump.

According to one embodiment of the invention, the laboratory automation system comprises a plurality of tubes which run from the pump to the pipetting device, and a plate with a tube guidance means, as described above and below. For example, the pump, the arm suspension means and/or the pipetting arm may bear the plate.

BRIEF DESCRIPTION OF THE FIGURES

Below, examples of embodiment of the invention will be described in detail with reference to the appended figures.

The reference numerals used in the figures and their meanings are listed in summary form in the list of reference numerals. In principle, identical or similar parts are provided with the same reference numerals.

DETAILED DESCRIPTION OF EXAMPLES OF EMBODIMENT

Figure 1:
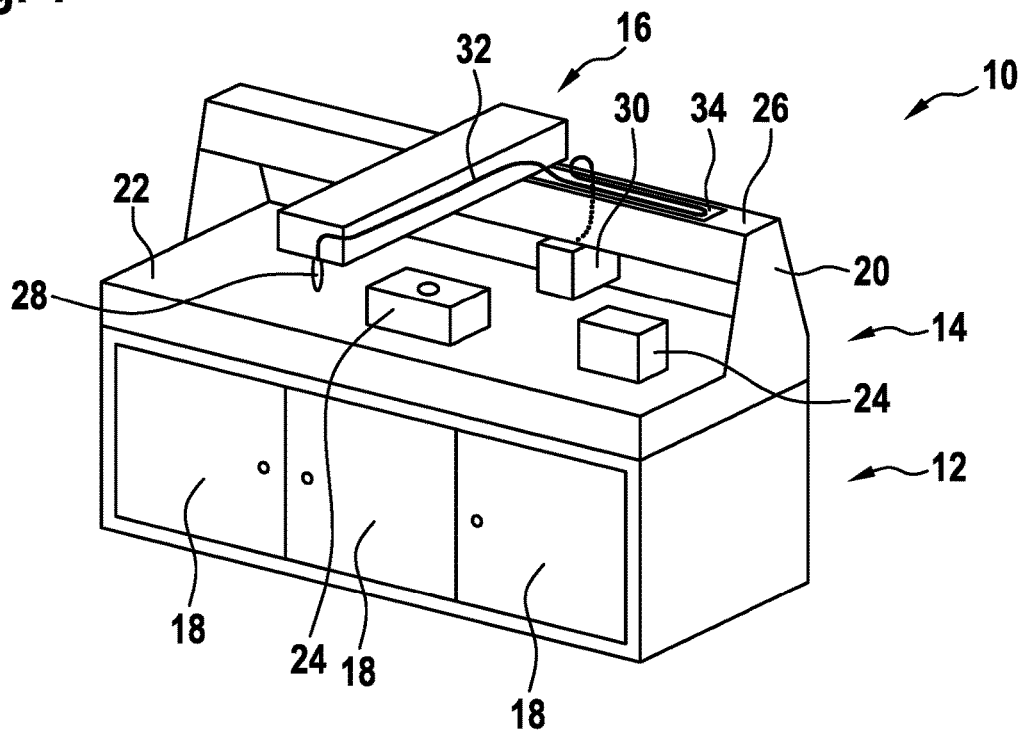
FIG. 1 is a schematic perspective view of a laboratory automation system according to one embodiment of the invention.

FIG. 1 shows a laboratory automation system 10 which comprises a substructure 12, a workbench 14 placed on the substructure 12, and a pipetting arm 16 fastened to the workbench 14. The substructure 12 may comprise one or more cabinets 18 and/or may hold the workbench 14 at a height so that an operator may have comfortable access to the workbench 14. The substructure 12 is optional. The laboratory automation system 10 may for example also be placed directly on a conventional laboratory bench.

The workbench 14 has a frame 20 on which a work surface 22 is fastened, on which in turn containers 24, such as containers for disposable pipetting tips, containers for samples, containers for chemicals, reagents, and/or pipetting plates etc. may be fixed or anchored.

The workbench 14 further has a rail 26 which is arranged above the work surface 22 and which runs parallel to the work surface. The pipetting arm 16 is fastened in movable manner to this rail 26. With the aid of one or more motors, the pipetting arm 16 may be moved along the rail 26 and/or a pipetting device 28 borne by the pipetting arm 16 may be moved in three dimensions above the work surface 22.

With a pump 30 integrated in the laboratory automation system 10, which pump is fastened for example to the workbench 14, liquids may be aspirated and dispensed from containers 24 with the pipetting device 28. The pipetting device 28 to this end may have a plurality of pipetting tips which are connected to the pump 30 by way of tubes 32.

The tubes 32 are guided from the pump via the rail 26, along the pipetting arm 16 to the pipetting device 28. In the rail 26, the tubes 32 may be guided through a drag chain 34 in order thus to compensate for the movements of the pipetting arm 16.

In the following figures, it is described how the tubes 32 may be fixed and/or fastened to different housing parts of the laboratory automation system 10.

Figure 2:
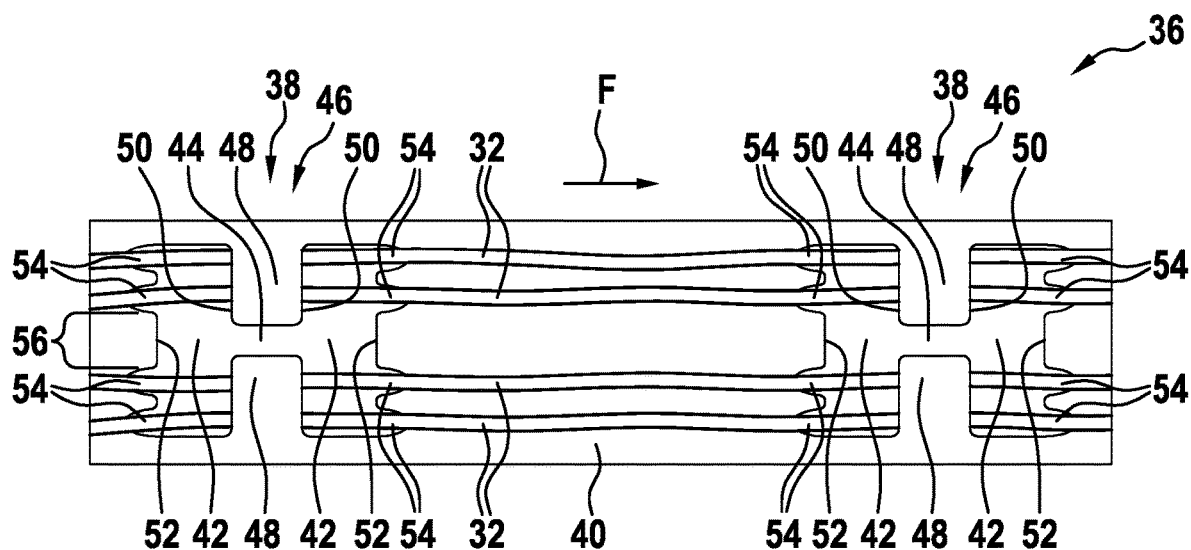
FIG. 2 is a plan view of a tube guidance means according to one embodiment of the invention.

FIG. 2 shows a tube guidance means (i.e., a tube guide) 36 with two guide openings 38 which are formed in a plate 40, for example a sheet. The plate 40 may be a casing of a component of the laboratory automation system 10 of FIG. 1, such as the pump 30 or the pipetting arm 16.

Each of the guide openings 38 has two partial openings 42 having a rectangular basic form which are connected together by way of a slot 44. The slot 44 runs in a direction of guidance F in which each of the tubes 32 is guided through the guide openings 38. Between the partial openings 42 there runs a land 46 through which the slot 44 runs in the direction of guidance F. In this manner, the land 46 comprises two tongues 48, which run towards each other transversely to the direction of guidance F. The tongues 48 clamp the tubes 32 in guide openings 38.

The land 46 provides an internal edge 50 for each of the partial openings 42. Opposite the edge 50 there is an outer edge 52, on which a plurality of cutouts 54 is formed. The edges 50 and/or the edges 52 run substantially parallel.

One tube 32 is placed in each case in the cutouts 54, which are arranged in a row along the edge 52. The cutouts 54 prevent movement of the tube 32 transversely to the direction of guidance F. The cutouts 54 have an opening which faces towards the land 46, and taper with increasing distance from the land 46.

The cutouts 54 in a transverse direction orthogonally to the direction of guidance F are arranged spaced apart from a slot region 56, so that the respective tube 32 runs behind the land 46 next to the slot 44 through the guide opening 38.

Figure 3:
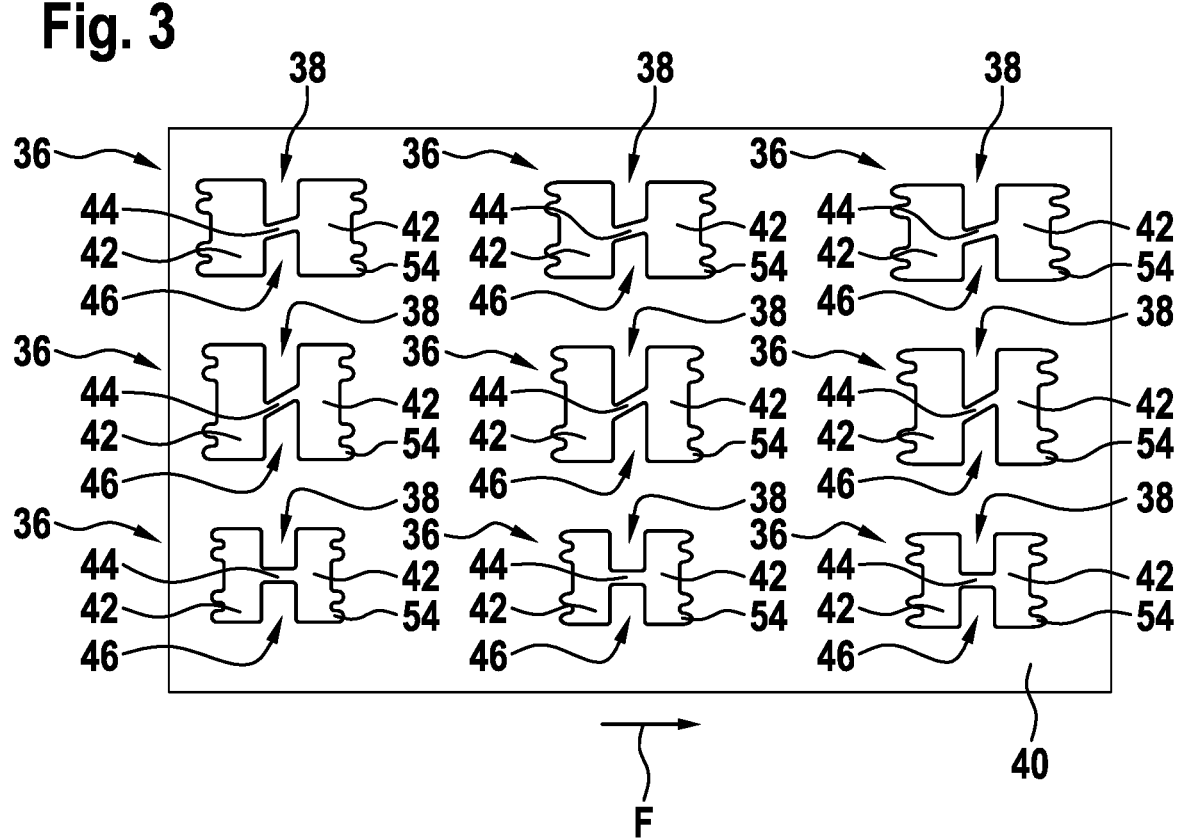
FIG. 3 shows outlines of tube guidance means according to embodiments of the invention.

FIG. 3 shows further embodiments of tube guidance means 36 or guide openings 38. It is shown that the cutouts 54 may be oval (left), triangular (middle) and parabolic (right). Further, the slot 44 may be oriented obliquely (top) or parallel to the direction of guidance F.

The clamping action of a guide opening 38 may be dependent on the plate thickness of the plate 40, the distance between the cutouts 54 in the direction F, the web width of the land 46 in the direction F and/or the ratio of the web width to the distance between the cutouts 54. FIG. 3 shows guide openings 38 which differ in the distance between the cutouts 54 and the web width.

Figure 4:
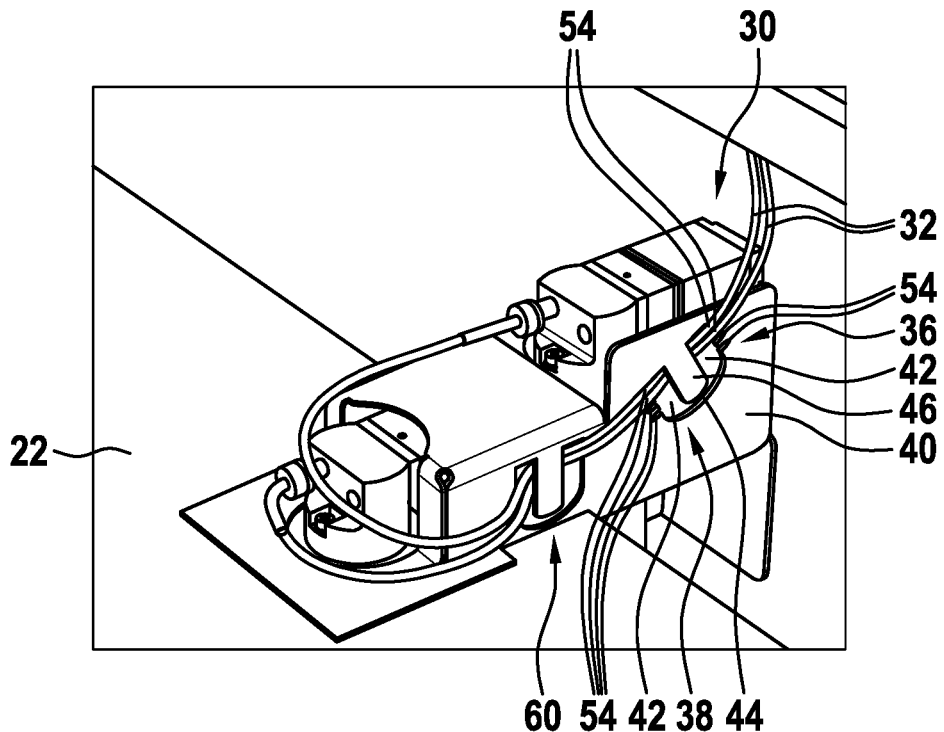
FIG. 4 is a perspective view of a pump with a tube guidance means according to one embodiment of the invention.

FIG. 4 shows more closely a pump 30, as may be integrated for example in the laboratory automation system 10 of FIG. 1. The pump 30 has a housing 58 which comprises the plate 40 with a tube guidance means 36. The tubes 32 are connected to the pump 30 and are then guided through one guide opening 60 without cutouts and one guide opening 38 with cutouts 54. Thence they run further on in the direction of the rail 26.

The guide opening 38 has a U-shaped slot 44 which is connected to a lateral edge of the partial openings 42.

Figure 5:
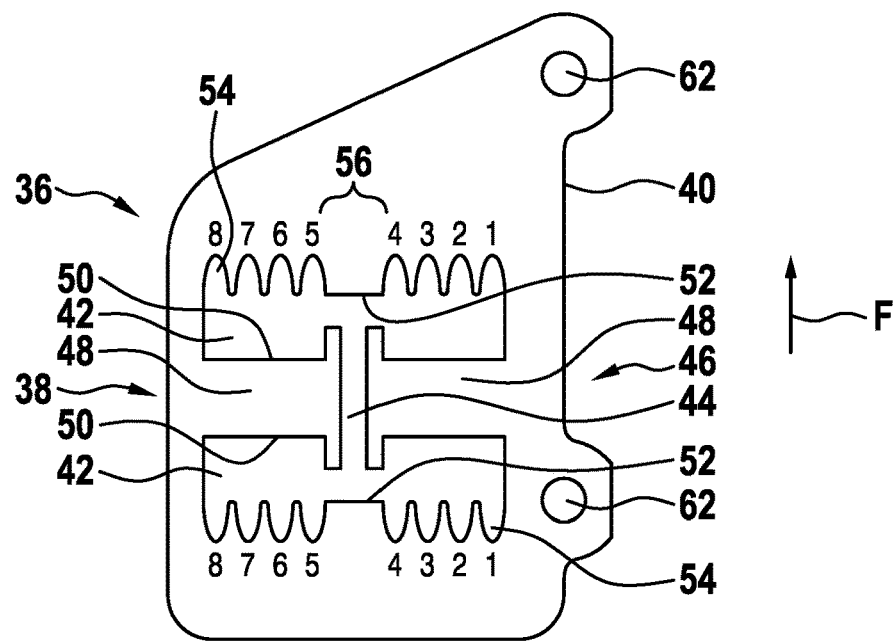
FIG. 5 is a plan view of a tube guidance means according to one embodiment of the invention.

FIG. 5 shows a tube guidance means 36 which is realised in a separate plate 40 which may be fastened to a further housing part by means of openings 62. In FIG. 5, the land 46 has tongues 48 which have an end which widens towards the slot 44. Further, it is shown that the cutouts 54 may be marked by means of openings in the plate 40 in the form of digits/letters.

Figure 6:
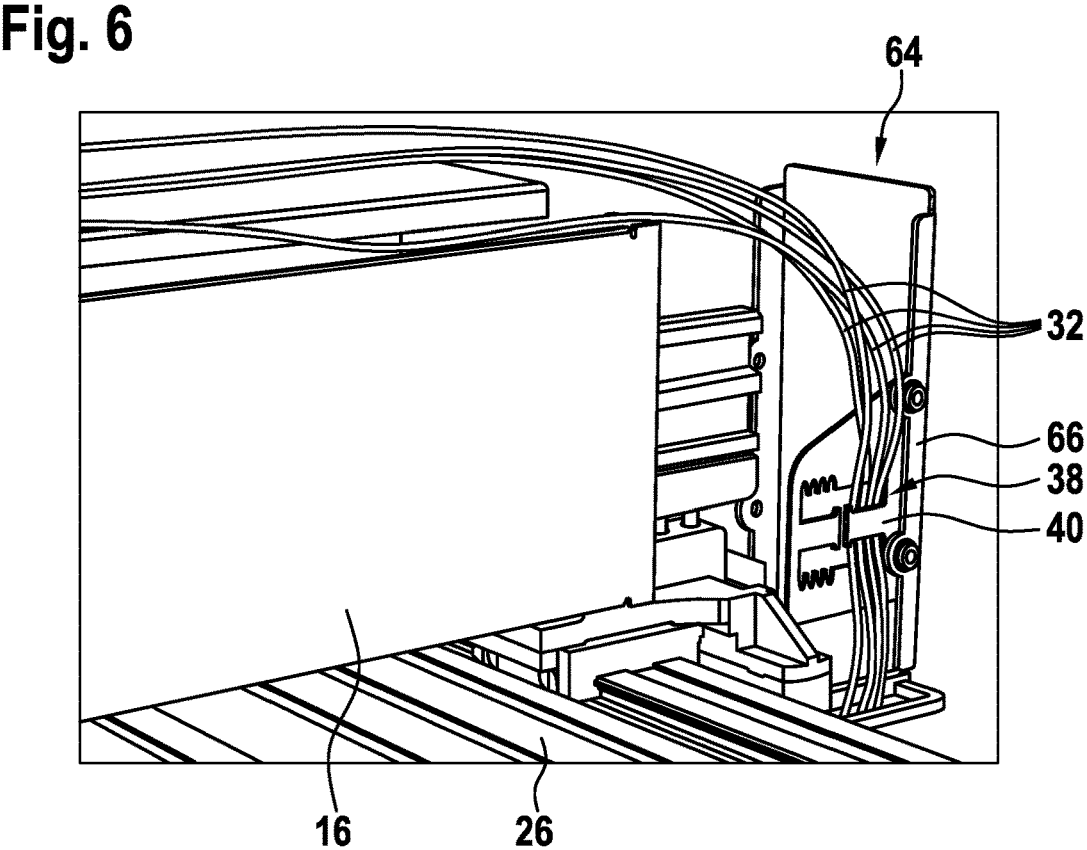
FIG. 6 is a perspective view of an arm suspension means with a tube guidance means according to one embodiment of the invention.

FIG. 6 shows more closely an arm suspension means 64, as may be integrated for example in the laboratory automation system 10 of FIG. 1. By way of the arm suspension means 64, the pipetting arm 16 may be connected in movable manner to the rail 26. The arm suspension means 64 comprises a housing 66 in which the plate 40 shown in FIG. 5 is integrated.

Figure 7:
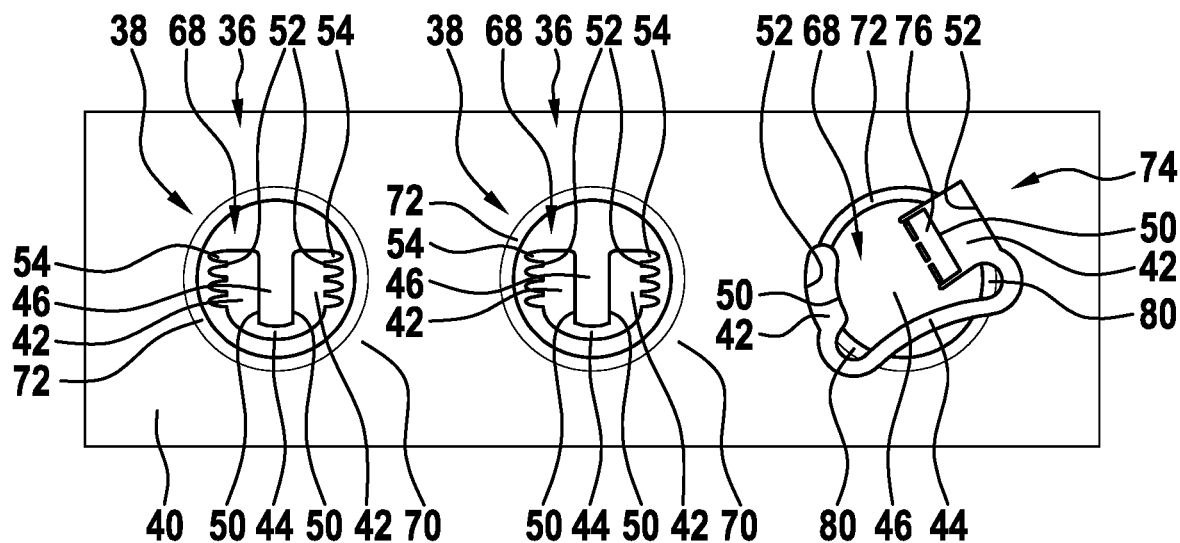
FIG. 7 is a plan view of a tube guidance means according to one embodiment of the invention.

FIG. 7 shows a further embodiment of a tube guidance means 36 or guide opening 38 which is formed twice in the plate 40 shown in FIG. 7. Here, the slot 44 is curved in a U-shape and connected to a lateral edge of the partial openings 42. The guide opening is arranged in a circular opening region 68 which is elevated with respect to a surrounding region 70. The region 68 and the region 70 are flat in each case and are connected by way of a transitional region 72 extending obliquely with respect to these regions.

The guide opening 38 and the land 46 are formed in the opening region 68 and are thus located in a different plane from a plane defined by the region 70.

FIG. 7 further shows a deflection opening 74 which is formed in the plate 40. The deflection opening 74 has two partial openings 42 arranged obliquely to each other which are separated by a land 46 and which are connected by a slot 44. The partial openings 42 are defined laterally by two tongues 80 which are provided by the land 46. In this manner, tubes cannot slip out of the partial openings 42. The deflection opening 74 is arranged in an opening region 68 of the plate 40 which is elevated with respect to the surrounding region 70. The land 46 in this case reaches into the transitional region 72 and the surrounding region 70. The tongues 80 may extend from the region 68 into the region 70. The slot 44 of the deflection opening 74 runs through the surrounding region 70, the transitional region 72 and the opening region 68. The three-dimensional form which is formed by the regions 70, 72, 74 may be produced with a cupping tool, as with the guide openings 38.

The partial openings 42 of the deflection opening 74 are arranged in the transitional region 72 between the regions 68, 70, so that their edges 50, 52 are arranged in different planes.

At the partial opening 42 at which the tubes 32 emerge from the deflection opening 74, on the inner edge 50 a wing 76 is present which is angled outwards with respect to the plane of the opening region 68. This may reduce the friction between the tubes 32 and the deflection opening 74.

Figure 8:
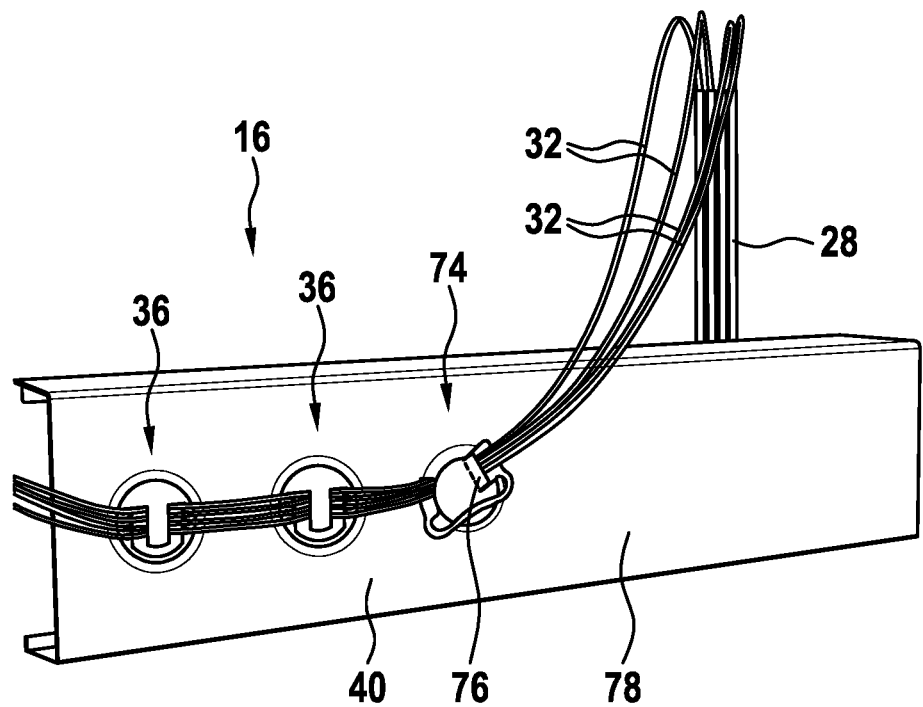
FIG. 8 is a perspective view of a pipetting arm with a tube guidance means according to one embodiment of the invention.

FIG. 8 shows more closely a pipetting arm 16, as may be integrated for example in the laboratory automation system 10 of FIG. 1. The pipetting arm 16 comprises a housing 78 with a plate 40, in which housing two tube guidance means 36 and a deflection opening 74 are formed, as are shown in FIG. 7. The tubes 32 run through the two tube guidance means 36, where they are fixed to the housing 78, and then through the deflection opening 74, in which they may move freely. Thence they run to the pipetting device 28, which may move upwards and downwards.

In addition, it should be pointed out that "comprising" does not rule out any other elements or steps, and "a" or "one" does not rule out a large number. Further, it should be pointed out that features or steps which have been described with reference to one of the above examples of embodiment

The invention claimed is:

1. A tube guide for a laboratory automation system, the tube guide comprising:
a plate having a guide opening;
the guide opening comprises two partial openings which are separated by a land and which are connected by a slot;
the partial openings have cutouts configured to guide a tube; and
the cutouts are located opposite each other on edges which face away from each other.

2. The tube guide according to claim 1, wherein:
the slot runs through a center of the land; or
the slot runs at one end of the land.

3. The tube guide according to claim 1, wherein the slot runs obliquely to a direction of guidance which is defined by two opposing cutouts for a tube.

4. The tube guide according to claim 1, wherein the slot is curved in a U-shape.

5. The tube guide according to claim 1, wherein the land widens towards the slot.

6. The tube guide according to claim 1, wherein the cutouts are arranged in a transverse direction spaced apart from a slot region of the land in which the slot is present.

7. The tube guide according to claim 1, wherein the cutouts widen towards the land.

8. The tube guide according to claim 1, wherein the cutouts are triangular, oval, parabolic, ellipsoidal and/or polygonal.

9. The tube guide according to claim 1, wherein:
the guide opening is arranged in an opening region of the plate which is elevated with respect to a surrounding region; and/or
the partial openings and the land are arranged in one plane.

10. The tube guide according to claim 1, wherein the plate has a plurality of guide openings.

11. The tube guide according to claim 1, wherein the plate has a deflection opening which has two partial openings arranged obliquely to each other which are separated by a land and which are connected by a slot.

12. The tube guide according to claim 11, wherein:
the deflection opening is arranged in an opening region of the plate which is elevated with respect to a surrounding region; and/or
the partial openings of the deflection opening are arranged in a transitional region between the opening region and the surrounding region, so that edges of the partial openings are arranged in different planes.

13. The tube guide according to claim 11, wherein the slot of the deflection opening runs through the transitional region and the opening region.

14. A laboratory automation system component, comprising:
a tube guide, comprising:
a plate having a guide opening;
the guide opening comprises two partial openings which are separated by a land and which are connected by a slot;
the partial openings have cutouts configured to guide a tube; and
the cutouts are located opposite each other on edges which face away from each other;
a plurality of tubes which are guided through the guide opening; and
the plate with the guide opening is a casing of the component.

15. A laboratory automation system, comprising:
a workbench;
a rail fastened to the workbench;
a pipetting arm fastened in movable manner to the rail by way of an arm suspension means, to which arm a pipetting device is fastened above the workbench;
a pump;
a plurality of tubes which run from the pump to the pipetting device; and
a plate with a tube guide for the plurality of tubes, the tube guide comprising:
a plate having a guide opening;
the guide opening comprises two partial openings which are separated by a land and which are connected by a slot;
the partial openings have cutouts configured to guide a tube; and
the cutouts are located opposite each other on edges which face away from each other.

* * * * *